United States Patent [19]

Ardaillon et al.

[11] Patent Number: 4,983,403

[45] Date of Patent: Jan. 8, 1991

[54] GRANULES FOR FEEDING RUMINANTS WITH AN ENZYMATICALLY DEGRADABLE COATING

[75] Inventors: Pierre Ardaillon, Saint-Priest; Paul Bourrain, Dardilly, both of France

[73] Assignee: Rhone-Poulenc Sante, Antony, France

[21] Appl. No.: 283,907

[22] Filed: Dec. 13, 1988

[30] Foreign Application Priority Data

Dec. 15, 1987 [FR] France ................... 87-17455

[51] Int. Cl.⁵ ............................... A23K 1/00
[52] U.S. Cl. .......................... 426/2; 426/72; 426/99; 426/302; 426/311; 426/656; 426/807
[58] Field of Search ............... 426/2, 98, 99, 302, 426/807, 72, 311, 656, 623, 630

[56] References Cited

U.S. PATENT DOCUMENTS

| | | |
|---|---|---|
| 3,119,738 | 1/1964 | Nichols . |
| 3,351,531 | 11/1967 | Noznick et al. ............ 426/98 |
| 4,066,754 | 1/1978 | Chou . |
| 4,713,245 | 12/1987 | Ando et al. ............ 426/2 |
| 4,832,967 | 5/1989 | Autant ............ 426/98 |

FOREIGN PATENT DOCUMENTS 1154294  9/1983  Canada ............ 426/69

OTHER PUBLICATIONS

S. I. Smith & J. A. Boling, "Lipid Coating As a Mode of Protecting Free Methionine From Ruminal Degradation", Journal of Animal Science, vol. 58, No. 1, 1984 pp. 187–193.

PCT Int. Pub. No. WO 86/01034 PCT/NL85/00032 Filed Jul. 31, 1985.

*Primary Examiner*—R. B. Penland
*Attorney, Agent, or Firm*—Stevens, Davis, Miller & Mosher

[57] ABSTRACT

Granules containing feed additives for ruminants are coated with an enzymatically degradable composition, consisting of: zein in combination with a non-water-soluble polymer and optionally a plasticizing agent, or zein in combination with a hydrophobic substance and optionally a non-water-soluble polymer.

18 Claims, No Drawings

GRANULES FOR FEEDING RUMINANTS WITH AN ENZYMATICALLY DEGRADABLE COATING

The present invention relates to protecting feed additives for ruminants from degradation in the rumen.

Many biologically active substances administered to ruminants undergo degradation in the rumen, and cannot therefore exert their full activity when they reach the digestive tract. It is consequently necessary to protect such biologically active substances against degradation in the rumen.

Hitherto, it has been proposed to coat biologically active substances with compositions which are stable in the rumen, in which the pH is in the region of 6, but permit the release of the active substance in the abomasum, in which the pH is in the region of 2. In general, such known coating compositions consist of a combination of a substance which is sensitive to pH changes, chosen, in particular, from synthetic basic copolymers, with a hydrophobic substance which can be chosen, e.g., from fatty acids or their derivatives and hydrophobic polymers, and the compositions form a continuous film around the biologically active substance. Such compositions are described, e.g., in French Patent Nos. FR 78/23,966 (2,401,620), FR 78/23,968 (2,401,621) or FR 81/18,954 (2,514,261).

The selection of compsitions which achieve the desired object is based on their difference in behavior according to the pH. The desired object is achieved when the coating composition is stable at a pH of not less than 5.5 for a long period (24 to 48 hours) and when it is rapidly degraded (a few minutes to a few hours) at a pH of not more then 3.5. As a result, coating compositions whose difference in behavior at pH 6 and pH 2 is small cannot be used in this way. Thus, coating compositions which consist of a non-water-soluble film-forming binder whose hydrophilicity is controlled and a substance which is sensitive to pH changes are described in European Patent Application No. EP 0,188,953. The comparative examples which are given show that, in the absence of one of the components of the compositions claimed, compositions are obtained which are unusable for the stated purpose, since they have comparable stabilities at pH 6 and at pH 2.

It has now been found, and this forms the subject of the present invention, that is it possible to protect biological active substances for ruminants by using coating mixtures which are stable both in a basic medium and in an acid medium so that the biologically active substance is released not in the abomasum but in the small intestine and retains its beneficial activity, the degradation of the coating being performed by the enzymes present in the intestine.

According to the present invention, a biologically active substance for the feeding of ruminants is provided in the form of a composition coated with a mixture which is stable in the rumen, which implies good resistance to the microbial flora and the emzymes of this environment; which is relatively stable in the abomasum, in which the pH is acid; and which is effectively degraded in the small intestine by the action of the enzymes encountered between the abomasum and the ileum.

The composition of the present invention comprises a ruminant feed additive coated with a mixture consisting of zein in combination with a non-water-soluble polymer; a hydrophobic substance; a non-water-soluble polymer and a plasticizing agent; or a hydrophobic substance and a non-water-soluble polymer.

The coating mixtures which are usable in the invention thus consist:

either of zein in combination with a non-water-soluble polymer which may be chosen from non-water-soluble cellulose ethers or esters, such as ethyl cellulose, cellulose acetate, cellulose propionate or cellulose acetate butyrate, and polyvinyl esters such as polyvinyl acetate, and optionally a plasticizing agent such as triacetin or propylene glycol, the zein generally representing from 50 to 90% by weight of the mixture and the plasticizing agent being capable of representing up to 10% by weight of the mixture;

or of zein in combination with a hydrophobic substance whose melting point is above 60° C., which may be chosen from fatty acids (e.g. stearic acid, behenic acid), fatty esters, fatty alcohols and mixtures thereof, and optionally with a non-water-soluble polymer chosen from non-water-soluble cellulose ethers or esters, such as ethyl cellulose, cellulose acetate, cellulose propionate or cellulose acetate butyrate, and polyvinyl esters such as polyvinyl acetate, the zein generally representing from 10 to 50% by weight of the mixture and the non-water-soluble polymer being capable of representing up to 10% by weight of the mixture.

In general, the mixtures of the first type are used for the coating of substances that are only sparingly soluble in water such as methionine, and those of the second type for water-soluble substances such as lysine hydrochloride.

It is particularly important to note that the coating mixtures which are used in the invention consist of substances which are known to be capable of being used in the food industry, which provides a considerable advantage over previously known compositions.

The coating mixtures of the invention are especially useful for coating active substances which are sensitive to degradation in an acid medium. Such substances are thus protected both at pH 6 (rumen) and at pH 2 (abomasum), and they are released only in the intensine (pH 7) as a result of the detection of the coating through the action of the enzymes present in the intestine.

The coating mixture used in the invention may be obtained by dispersing or dissolving zein in a solution or a dispersion of the non-water-soluble polymer and/or of the hydrophobic substance, and optionally, according to circumstances, the plasticizing agent, in an organic solvent or in a mixture of suitable organic solvents which are chosen in accordance with the specific nature of the constituents. In general, the coating mixture is obtained after evaporation of the solvent or solvents.

The coating mixtures are especially useful for protecting various therapeutic or nutrient substances such as medicinal products, vitamins or amino acids, intended for oral administration to ruminants. The coated substances are generally mixed with the animals' feed.

The coated substances are generally granules in the form of microcapsules consiting of a central core of the biologically active substance surrounded by a continuous film of the coating mixture. However, the active substances can also be dispersed in the coating mixture. In general, the coating represents 5 to 60% by weight of the granule or dispersion.

Such granules may be obtained by the use of known techniques. Depending on the nature of the coating mixture, use is made either of techniques of extrusion or spraying of solutions or emulsions in a fluidized bed, or of techniques of encapsulation in a molten or semi-molten medium, or of techniques of coating in a liquid medium such as coacervation.

The granules obtained according to the present invention are stable on storage and on handling, do not deteriorate during the preparation of feeds and are not destroyed when they are eaten by the animals, and especially by crushing or by grinding during mastication.

The size of the granules will depend on the use which is made of them, and will be determined more especially according to the animal for which they are intended.

It is possible to coat active substances so as to obtain granules whose size is between 0.1 and 5 mm.

Granules which contain, as active substances, methionine, lysine or vitamins (e.g. Vitamin A), the role of which is very important in animal nutrition and more especially in that of ruminants, are of very special value.

The examples which follow illustrate the present invention.

EXAMPLE 1

Granules of methionine coated with a coating consisting of zein (69.2,), ethyl cellulose N22 (Hercules) (23%) and triacetin (7.7%) are prepared by the technique of encapsulation by spray-coating (described, e.g., in European Patent Application No. EP 188,953). The titre of methionine in the coated granules is 72%.

Separately, by way of comparison, granules of methionine coated with the folowing compsitions are prepared:

Granules A: Ethyl cellulose N100 (Hercules) (80%)
Styrene/2-vinylpyridine (30:70) copolymer (20%)
The titre of methionine in the coated granules is 70%.
Granules B: Ethyl cellulose N100 (Hercules) (58.3%)
Styrene/2-vinylpyridine (30:70) copolymer (25%)
Propylene glycol (16.7%)
The titre of methionine in the coated granules is 73%.

The different coated granules thereby prepared are subjected to in vitro and in vivo tests.

(1) In vitro test

The release of the methionine present in the granules obtained is examined, under specified conditions, by stirring a known quantity of granules in a buffered medium maintained at constant pH at a temperature of 40° C. The rates of release of a sample subjected to different pH values are compared.

The results obtained are collated in Table 1.

TABLE 1

| Product | Titre of methionine | % of methionine released | | | | | | |
|---|---|---|---|---|---|---|---|---|
| | | at pH 6 after | | at pH 2 after | | | | |
| | | 6 hours | 24 hours | ½ h | 1 h | 2 h | 5 h | 7 h |
| Granules according to Example 1 | 72 | 9 | 19 | | | | 5 | 12 |
| Granules A | 70 | 3 | 5.5 | 2 | | | 22 | |
| Granules B | 73 | | | 1.3 | 2.5 | 3.6 | 6 | 8.5 |

(2) In vivo test

The resistance of the granules to a period of time spent in the rumen, in the abomasum and then in the small intestine in sheep is determined by measuring the total quantity of nitrogen which has disappeared from the sachets after each of the three successive stages.

2.1 Digestion in the rumen

Nylon sachets (46-micron square mesh) each containing approximately 3 g of coated granules, weighed accurately, are incubated for 12 hours in the rumen of 2 sheep on the basis of 2 sachets per product and per sheep.

After incubation in the rumen, the sachets are washed with cold water and then lyophilized for 48 hours. The sachets are weighed and the quantity of granules which has disappeared is determined. The residues are then removed from the sachets and sampled in duplicate for the assay of total nitrogen.

The remaining residues are gathered together according to product type, and placed in new nylon sachets intended for incubation in the abomasum.

2.2 Digestion in the abomasum

Three nylon sachets (46-micron square mesh), the size of which is substantially half that of the sachets used for digestion in the rumen, containing approximately 0.5 g of residue, are used for each incubation period and for each product tested.

These sachets are introduced, attached to a thread into the abomasum of 3 sheep equipped with an abomasum cannula (internal diameter 28 mm) and subjected to the same feed diet on the basis of 1 sachet per sheep and per product.

After incubation for 0.5 hour, 2 hours and 4 hours, the sachets are washed, lyophilized and weighed. The residues are on the one hand sampled for the assay of nitrogen, and on the other hand used for studying the digestion in the small intestine.

2.3 Digestion in the small intestine

The residues obtained above are grouped together according to incubation time and to product. They are introduced into micro-sachets (discs 20 mm in diameter) of nylon (46-micron square mesh) on the basis of 200 mg of residue per sachet and 3 sachets per incubation time.

These sachets are introduced at the entry to the small intestine (duodenum) of three sheep subjected to the same feed diet and equipped with a simple cannula at duodenal level (5 cm for pylorus, 12 mm in internal diameter) and a re-entrant cannula (18 mm in internal diameter) at the end of the small intestine (terminal ileum).

The residues of each type of coating are studied in pairs during 2 series of measurements, each animal receiving 1 sachet of each of the 6 treatments (2 coatings × 3 incubation times in the abomasum).

The 6 sachets per animal are introduced at 15-minute intervals. 3 hours after the beginning of the introduction, the re-entrant cannula is opened and the ileal contents discharge freely outside the animal. The sachets are expelled after a transit period varying from 3.5 to 8 hours. They are immediately collected and analysed as above.

The results obtained are collated in Table 2.

TABLE 2

RELEASE OF THE PRODUCTS IN DIFFERENT COMPARTMENTS OF THE DIGESTIVE TRACT OF THE SHEEP

| | RUMEN | | |
|---|---|---|---|
| Methionine | Time h | Number of tests | Record of total N % disappeared |
| Product according to Example 1 | 12 | 4 | 6.64 ± 0.49 |
| Granules A | 12 | 4 | 2.19 ± 0.68 |
| Granules B | 12 | 4 | 6.51 ± 0.51 |
| | ABOMASUM | | |
| | Time | Number | Record of total N |

TABLE 2-continued
RELEASE OF THE PRODUCTS IN DIFFERENT COMPARTMENTS OF THE DIGESTIVE TRACT OF THE SHEEP

| Methionine | h | of tests | % disappeared |
|---|---|---|---|
| Product according to Example 1 | 0.5 | 3 | 6.13 ± 0.06 |
| | 2 | 3 | 11.17 ± 1.23 |
| | 4 | 3 | 14.82 ± 0.13 |
| Granules A | 0.5 | 3 | 0 |
| | 2 | 3 | 2.64 ± 0.19 |
| | 4 | 3 | 6.64 ± 0.57 |
| Granules B | 0.5 | 3 | 1.37 ± 0.17 |
| | 2 | 3 | 1.24 ± 0.11 |
| | 4 | 3 | 2.07 ± 0.07 |

SMALL INTESTINE

| Methionine | Number of tests | Record of total N % disappeared |
|---|---|---|
| Product according to Example 1 | 2 | 95.70 ± 1.53 |
| | 3 | 96.57 ± 3.72 |
| | 3 | 95.72 ± 4.58 |
| Granules A | 3 | 7.06 ± 2.69 |
| | 3 | 6.66 ± 2.26 |
| | 2 | 2.51 ± 0.47 |
| Granules B | 3 | 0 |
| | 3 | 0.58 ± 1.00 |
| | 3 | 0.69 ± 0.62 |

EXAMPLE 2

Zein (22 g) and pure stearic acid (88 g) are dissolved in a mixture of dichloromethane (500 cc) and absolute ethanol (500 cc).

The solution obtained is sprayed, by the "spray-coating" technique, onto methionine (350 g) in the form of granules whose average diameter is between 0.5 and 0.63 mm.

Coated granules whose titre of methionine is 74.5% are thereby obtained.

The quantity of methionine released from the granules after 24 hours at 40° C. in a buffered aqueous medium at pH 6 is 6%, and at pH 2 is 7%.

After a period of 48 hours spent in the rumen of ewes, the level of residual methionine is 68.0±6%.

EXAMPLE 3

Zein (14 g), pure stearic acid (88 g) and ethyl cellulose N 22 (8 g) are dissolved in a mixture of dichloromethane (500 cc) and absolute ethanol (500 cc).

The solution obtained is sprayed, by the "spray-coating" technique, onto lysine hydrochloride (350 g) in the form of granules whose average diameter is in the region of 0.8 mm.

Coated granules whose titre of lysine hydrochloride is 69.4% are thereby obtained.

The quantity of lysine hydrochloride released from the granules after 24 hours at 40° C. in a buffered medium at pH 6 is 2.6%, and at pH 2 is 6%.

After a period of 48 hours spent in the rumen of ewes, the level of residual lysine hydrochloride is 78.0±2%.

We claim:

1. Composition for feeding an additive to ruminants which is stable in the rumen and in the abomasum and which is degraded by the enzymes of the intestine thereby releasing the additive, in the form of granules consisting essentially of a ruminant feed additive core provided with a coating in a single layer of a mixture consisting of 50 to 90% by weight of zein in combination with a non-water-soluble polymer and 0 to 10% by weight of a plasticizing agent; or of 10 to 50% by weight of zein in combination with a hydrophobic substance and 0 to 10% by weight of a non-water-soluble polymer, the said mixture constituting 5 to 60% by weight of the granules.

2. Composition according to claim 1 in which the said mixture consists of 50 to 90% by weight of zein in combination with a non-water-soluble polymer chosen from non-water-soluble cellulose ethers or esters and polyvinyl esters, and 0 to 10% by weight of a plasticizing agent.

3. Composition according to claim 2 in which the plasiticizing agent is triacetin or propylene glycol.

4. Composition according to claim 2 in which the non-water-soluble polymer is ethyl cellulose, cellulose acetate, cellulose propionate, cellulose acetate butyrate, or polyvinyl acetate.

5. Composition according to claim 1 in which the said mixture consists of 10 to 50% by weight of zein in combination with a hydrophobic substance whose melting point is above 60° C and 0 to 10% by weight of a non-water-soluble polymer chosen from non-water-soluble cellulose ethers or esters and polyvinyl esters.

6. Composition according to claim 5 in which the hydrophobic substance is a fatty acid, fatty ester, fatty alcohol or mixture thereof.

7. Composition according to claim 5 in which the non-water-soluble polymer is ethyl cellulose, cellulose acetate, cellulose propionate, cellulose acetate butyrate, or polyvinyl acetate.

8. Composition according to claim 1 in which the ruminant feed additive is a veterinary medicine, a vitamin, or an amino acid.

9. Composition according to claim 1 in which the ruminant feed additive is methionine or lysine.

10. Method for feeding to ruminants an additive composition which is stable in the rumen and in the abomasum and which is degraded by the enzymes of the intestine thereby releasing the additive, which consists essentially of feeding to said ruminants a ruminant feed additive provided with a coating in a single layer mixture consisting of 50 to 90% by weight of zein in combination with a non-water-soluble polymer and 0 to 10% by weight of a plasticizing agent; or of 10 to 50% by weight of zein in combination with a hydrophobic substance and 0 to 10% by weight of a non-water-soluble polymer, the said mixture constituting 5 to 60% by weight of the granules.

11. Method according to claim 10 in which the said feed additive is coated with a mixture consisting of 50 to 90% by weight of zein in combination with a non-water-soluble polymer chosen from non-water-soluble cellulose ethers or esters and polyvinyl esters, and 0 to 10% by weight of a plasticizing agent.

12. Method according to claim 11 in which the plasticizing agent is triacetin or propylene glycol.

13. Method according to claim 11 in which the non-water-soluble polymer is ethyl cellulose, cellulose acetate, cellulose propionate, cellulose acetate butyrate, or polyvinyl acetate.

14. Method according to claim 10 in which the said feed additive is coated with a mixture consisting of 10 to 50% by weight of zein in combination with a hydrophobic substance whose melting point is above 60° C. and 0 to 10% by weight of a non-water-soluble polymer chosen from non-water-soluble cellulose ethers or esters and polyvinyl esters.

15. Method according to claim 14 in which the hydrophobic substance is a fatty acid, fatty acid, fatty ester, fatty alcohol or mixture thereof.

16. Method according to claim 14 in which the non-water-soluble polymer is ethyl cellulose, cellulose acetate, cellulose propionate, cellulose acetate butyrate, or polyvinyl acetate.

17. Method according to claim 10 in which the ruminant feed additive is a veterinary medicine, a vitamin, or an amino acid.

18. Method according to claim 10 in which the ruminant feed additive is methionine or lysine.

* * * * *